(12) United States Patent
Mazurenko

(10) Patent No.: US 8,184,300 B2
(45) Date of Patent: May 22, 2012

(54) METHOD AND APPARATUS FOR REDUCING PROBE WAVELENGTH IN LASER EXCITED SURFACE ACOUSTIC WAVE SPECTROSCOPY

(75) Inventor: Alexander Mazurenko, Dedham, MA (US)

(73) Assignee: Alexander Mazurenko, Dedham, MA (US)

( * ) Notice: Subject to any disclaimer, the term of this patent is extended or adjusted under 35 U.S.C. 154(b) by 709 days.

(21) Appl. No.: 11/721,645

(22) PCT Filed: Dec. 8, 2005

(86) PCT No.: PCT/IB2005/054142
§ 371 (c)(1),
(2), (4) Date: Jul. 1, 2009

(87) PCT Pub. No.: WO2006/064428
PCT Pub. Date: Jun. 22, 2006

(65) Prior Publication Data
US 2009/0303496 A1     Dec. 10, 2009

Related U.S. Application Data

(60) Provisional application No. 60/635,680, filed on Dec. 13, 2004.

(51) Int. Cl.
*G01B 9/02* (2006.01)
*G01B 11/28* (2006.01)
(52) U.S. Cl. ......................... 356/503; 356/521; 356/630

(58) Field of Classification Search .................. 356/503, 356/504, 630, 632, 521
See application file for complete search history.

(56) References Cited

U.S. PATENT DOCUMENTS

| | | | | |
|---|---|---|---|---|
| 5,633,711 A * | 5/1997 | Nelson et al. | .................. | 356/318 |
| 6,069,703 A * | 5/2000 | Banet et al. | ................... | 356/432 |
| 6,795,198 B1 * | 9/2004 | Fuchs et al. | .................... | 356/521 |
| 6,935,935 B2 * | 8/2005 | Tada et al. | ..................... | 451/285 |
| 2002/0185634 A1 * | 12/2002 | Marder et al. | ................ | 252/582 |
| 2003/0009104 A1 * | 1/2003 | Hyman et al. | ................ | 600/476 |

* cited by examiner

*Primary Examiner* — Patrick J Connolly
(74) *Attorney, Agent, or Firm* — Goodwin Procter LLP

(57) ABSTRACT

The penetration depth of surface acoustic wave scales with wavelength. To measure thinner films using impulse stimulated thermal scattering (ISTS) it is advantageous to reduce the measurement wavelength to on the order of 1 micron. One way to reduce the measurement wavelength is to employ a high numerical aperture lens to converge an excitation and probe laser beam in an optical system at wider angles. While doing this, the increased optical/mechanical tolerances can be reduced by fine-tuning the phase between an excitation laser pattern and a probe laser pattern by adjusting either a neutral-density filter or matching plate for a particular wavelength. Blocking unwanted diffraction order beams generated by the optical system with a specialized design beam block plate is needed to retain the long wavelength capability.

9 Claims, 5 Drawing Sheets

METHOD AND APPARATUS FOR REDUCING PROBE WAVELENGTH IN LASER EXCITED SURFACE ACOUSTIC WAVE SPECTROSCOPY

CROSS-REFERENCE TO RELATED APPLICATIONS

This application is the U.S. national stage application of International (PCT) Patent Application Serial No. PCT/IB/ 2005/054142, filed Dec. 8, 2005, which claims the benefit of priority to U.S. Application No. 60/635,680, filed Dec. 13, 2004. The entire disclosures of these two applications are incorporated herein by reference in their entireties.

This invention relates to a method and apparatus for measuring properties (e.g., thickness) of thin layers (e.g., metal films) contained in a structure.

During fabrication of microelectronic devices, thin films of metals and metal alloys are deposited on silicon wafers and used as electrical conductors, adhesion-promoting layers, and diffusion barriers. Thickness variations in these films can modify their electrical and mechanical properties, thereby affecting the performance of the integrated circuit.

During fabrication of the integrated circuit, films are deposited to have a thickness of within a few percent of their target value. Because of these rigid tolerances, film thickness is often measured as a quality-control parameter during and/or after the integrated circuit's fabrication. Non-contact, non-destructive measurement techniques (e.g., optical techniques) are preferred because they can measure patterned "product" samples, rather than sacrificial "monitor" samples. Measurement of product samples accurately indicates errors in fabrication processes and additionally reduces costs associated with monitor samples.

Optical methods for measuring thin, opaque films have been described. For example, U.S. Pat. Nos. 5,633,711 (entitled MEASUREMENT OF MATERIAL PROPERTIES WITH OPTICALLY INDUCED PHONONS), 5,546,811 (entitled OPTICAL MEASUREMENT OF STRESS IN THIN FILM SAMPLES), 5,672,830 (entitled MEASURING ANISOTROPIC MATERIALS IN THIN FILMS), and U.S. Ser. No. 08/783,046 (entitled METHOD AND DEVICE FOR MEASURING THE THICKNESS OF OPAQUE AND TRANSPARENT FILMS), all incorporated herein by reference, describe an optical measurement technique called impulsive stimulated thermal scattering ("ISTS"). In ISTS two optical pulses are overlapped on a sample to form a spatially and temporally varying excitation pattern that launches counter-propagating acoustic waves. U.S. Pat. No. 5,734,470 (entitled DEVICE AND METHOD FOR TIME-RESOLVED OPTICAL MEASUREMENTS) describes how a single pulse passes through a diffractive mask, e.g. a phase mask, to project a pattern of stripes using a pulsed excitation laser. Almost instantaneous heating up of the illuminated areas creates a pattern of elastic stress that oscillates as counter-propagating surface acoustic waves. These patents are also incorporated herein by reference.

In ISTS the acoustic waves form a "transient grating" that includes an alternating series of peaks and nulls. A probe pulse irradiates the grating, and is diffracted to form a pair of signal beams (in addition to the directly reflected beam). One or both of the signal beams are detected and analyzed to measure a property of the sample.

FIG. 1 depicts a prior art optical system 1. Laser 10 generates an optical excitation pulse 11 which is split by a phase grating 12 into sub pulses 11', 11". Sub pulses 11', 11" pass through a lens 13. The collimated sub pulses 11', 11" are focused onto the surface of a sample 15 by a second lens 14. This forms the transient grating. Probe laser 16 generates a probe beam 17 which is split into probe beam 17 and reference beam 17' by phase grating 12. Lens 13 collimates probe beam 17 and reference beam 17'. Flat glass plates 18' and 18 are a neutral density filter and a matching plate, respectively. Plates 18, 18' ensure that the transient grating is in phase with the pattern formed by the probe beam 17/reference beam 17' pair. Plates 18, 18' can be tilted to a single tilt position for a range of excitation wavelengths to adjust the phases of the probe beam 17 and/or the reference beam 17' to align the transient grating phase with the pattern formed by the probe beam 17/reference beam 17' pair. Lens 14 focuses the probe beam 17 and reference beam 17' onto the transient grating. The transient grating diffracts a portion of the probe beam 17 and reflects a portion of the probe beam 17. Detector 19 detects the diffracted and reflected portions of probe beam 17.

A disadvantage of the prior art optical system is that the measurement wavelength (the period of the transient grating pattern excited by the excitation laser) is relatively long. The penetration depth of the surface acoustic wave scales with wavelength. Prior art optical systems have minimum measurement wavelength of 4 microns. Since each wiring level of a typical modern integrated circuit is on the order of 1 micron thick, it is advantageous to reduce the measurement wavelength to ~1 micron. The invention proposes to reduce the measurement wavelength, for example to 1.2 µm. This can be achieved in one exemplary aspect by providing an apparatus including: a first light source that generates an optical excitation pulse; an optical system aligned to receive the optical excitation pulse, separate it into at least two optical pulses and focus at least one pulse onto a surface of a sample to form an excitation pattern with at least one spatial phase and at least one spatial period; a second light source that generates a probe beam that diffracts off the sample; an optical detector that detects the diffracted portion of the probe beam to generate a signal; and a processor configured to process the signal from the optical detector to determine a property of the sample, and the optical system permits excitation patters with measurement wavelengths between 1.2 and 11 microns.

In one embodiment, the optical system includes an achromat doublet lens that includes a low refractive index element and a high refractive index element.

In another embodiment, the achromat doublet lens includes at least one element made out of gradient-index glass or at least one surface of the lens is aspheric.

In another embodiment, the achromat doublet lens is truncated with a plane cut parallel to the lens axis in order to allow better packaging of other device components (e.g. a vision system). The one-cemented block design of the doublet lens simplifies its mounting and alignment.

In another embodiment, the optical system includes at least two plates, and wherein the tilt of one of the at least two plates can be adjusted in response to a particular excitation wavelength.

In one embodiment, at least one of the two plates is attached to a mount which is attached to an electro-mechanical assembly which adjusts the tilt of the plate to which it is attached.

In another embodiment, the optical system includes a phase grating which produces multiple diffraction order beams, and a beam block configured to block at least one excitation beam beyond the +1st and −1st diffraction orders.

In another aspect a method of measuring a sample includes the steps of: irradiating a portion of the sample with an excitation pattern having at least one spatial phase and spatial period; diffracting a portion of a probe beam off a surface of the sample; detecting the diffracted portion of the probe beam with an optical detector to generate a light-induced signal; processing the light-induced signal to determine a property of the sample, wherein the irradiating and diffracting steps further comprise reducing a minimum probing wavelength to between 1 and 1.2 µm.

In one embodiment, the minimum probing wavelength reduces to between 1 and 1.2 µm by employing an achromat doublet lens with at least one gradient-index-glass element and/or with at least one aspheric surface, adjusting the tilt of at least one plate in response to a particular excitation wavelength, and/or employing a beam block configured to block at least one excitation beam beyond the +1st and −1st excitation order.

The invention provides many advantages, some of which are elucidated with reference to the embodiments below.

Figure 1:
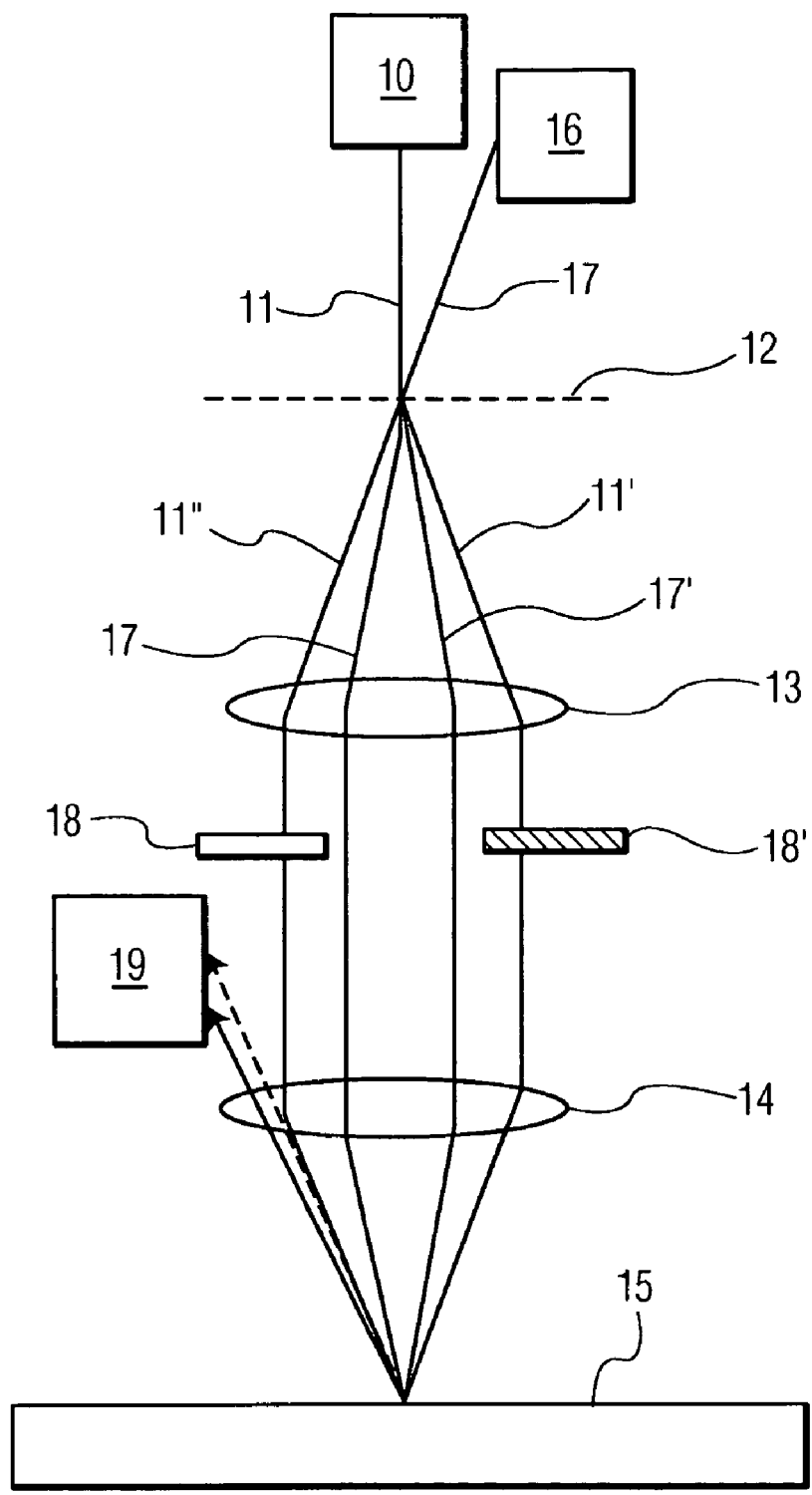
FIG. 1 depicts a prior art optical system.
Figure 2:
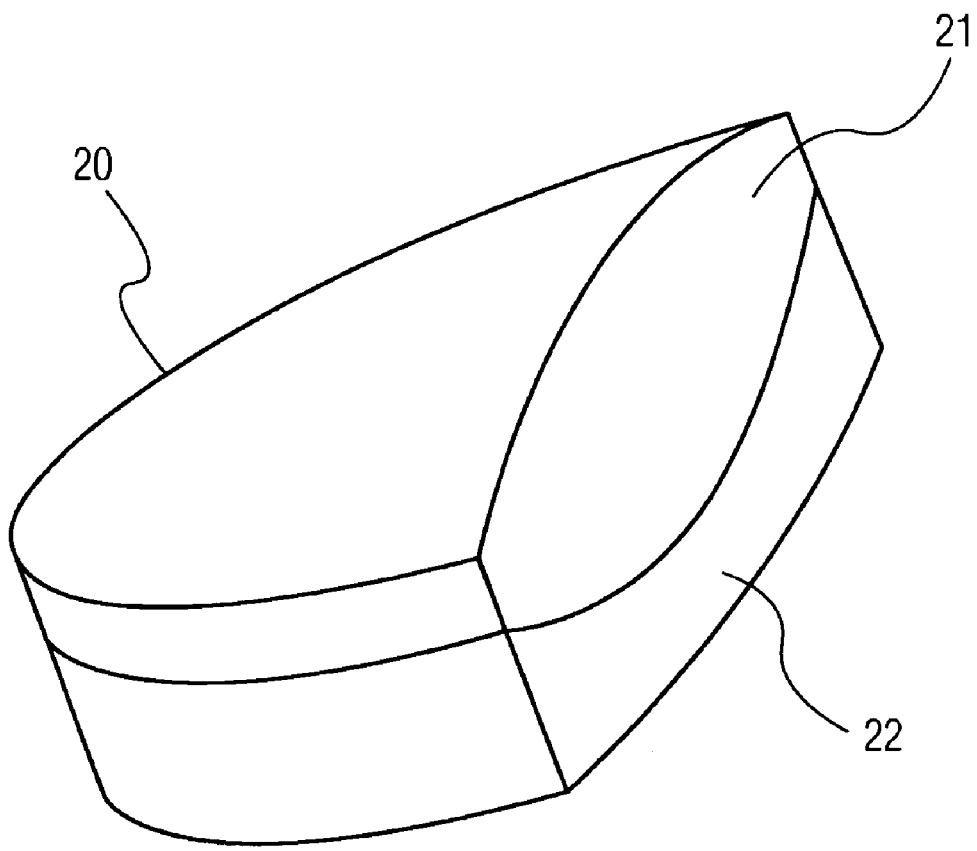
FIG. 2 depicts a truncated high numerical aperture doublet lens.

FIG. 2 depicts a high numerical aperture lens 20 which can be used in place of lens 14 of FIG. 1. High numerical aperture lens 20 has, for example, two components: high-refraction index glass element 21 and low-refraction index glass element 22. Elements 21 and 22 are cemented together to form an achromat doublet lens. To reduce the measurement wavelength, for example, gradient-index glass (i.e., glass in which index of refraction is not uniform but rather increases, typically along the lens axis; selecting the glass with a particular rate of index change allows increasing the numerical aperture of the lens without sacrificing its performance) is used to form the low-refraction index element 22. Using gradient-index glass to form element 22 allows for approximately double gain in numerical aperture. Another approach is to make at least one surface of at least one element aspheric (i.e., non-spherical surface, typically described by some mathematical equation, optimized to achieve the best possible performance). A single aspheric outside surface allows for a greater than three times gain in numerical aperture. The higher numerical aperture of lens 20 converges excitation sub beams 11', 11" and probe beam 17/reference beam 17' pair of FIG. 1 at wider angles than the prior art lens. This reduces the spacing of the projected excitation pattern that generates the transient grating. The spacing of the excitation pattern determines the wavelengths of the launched surface acoustic wave.

In either approach, lens 20 is truncated (for example, with a plane cut parallel to the lens axis and located within a few millimeters of it). This allows better placement of a vision system (not shown) of the optical system 1 of FIG. 1.

Figure 3:
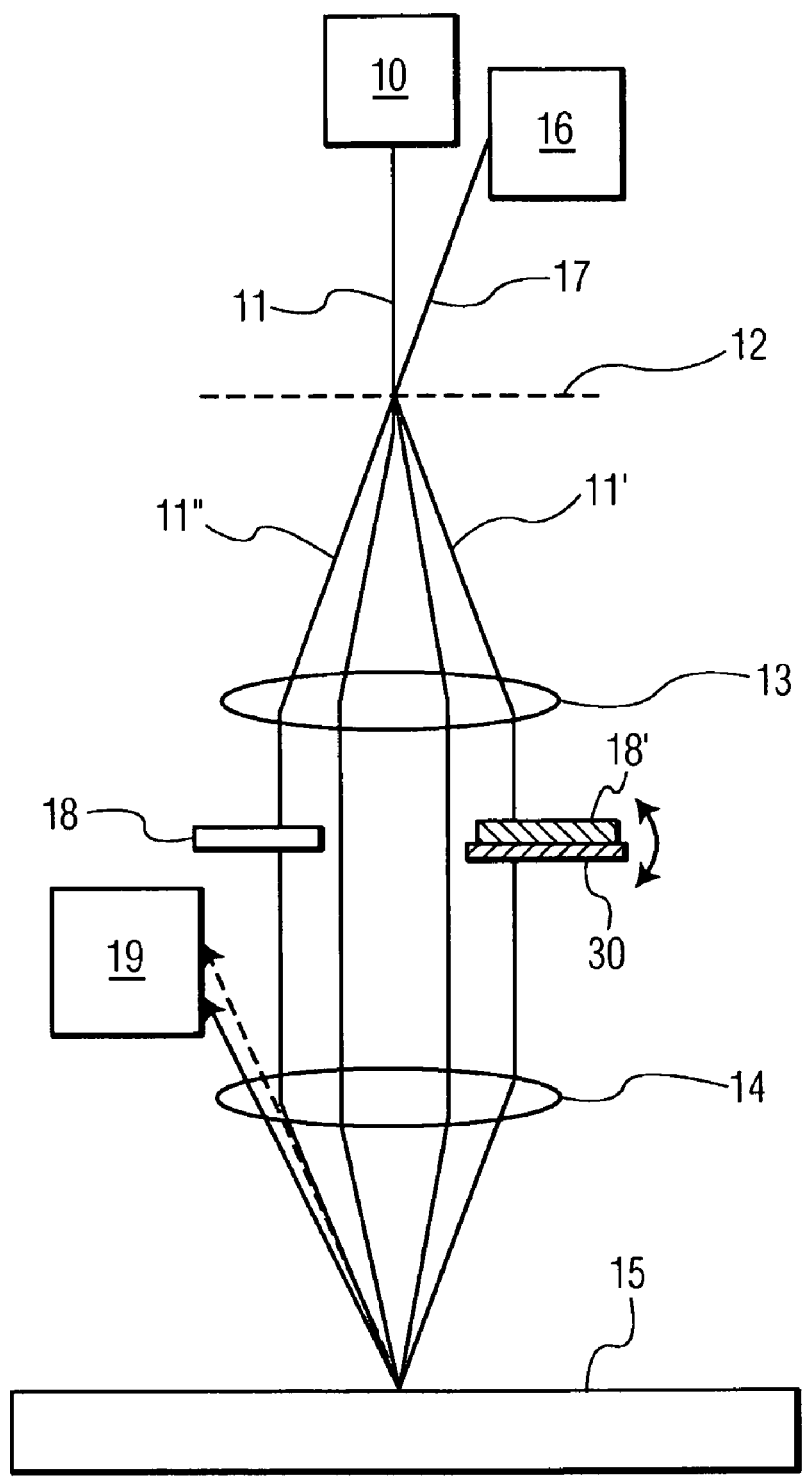
FIG. 3 depicts an optical system with individually adjustable glass plates.

An additional method of reducing the probing wavelength is to include at least one automatically adjustable glass plate that can be adjusted at each excitation wavelength, as depicted in FIG. 3. Plates 18, 18' of FIG. 1 ensure that the transient grating is in phase with the pattern formed by the probe beam 17/reference beam 17' pair. According to the prior art, plate 18' can be individually tilted to a single tilt position in order to adjust the phases of the probe beam 17 and/or the reference beam 17'. This aligns the transient grating phase with the pattern formed by the probe beam 17/reference beam 17' pair. The excitation pattern should be in phase with the pattern of interference formed by the probe beam 17/reference beam 17' pair for optical system 1 to work efficiently.

As depicted in FIG. 3, if the beam layout is symmetric both patterns should be in phase by design. However, in practice it has been observed that slight misalignments in the system render the patterns out of phase. Given the extended wavelength range it is difficult to find a single tilt position of plates 18, 18' which satisfies the requirements of matching excitation pattern phase with the pattern of interference formed by the probe beam 17/reference beam 17' pair over a whole range of wavelengths. The range of wavelengths imposes very strict tolerances on both the optical components' quality and assembly.

As shown in FIG. 3, plate 18' tilt is capable of being individually adjustable in any direction for each excitation wavelength. A mount 30 can enact individual adjustments at various wavelengths with an electric stepper motor or any other electro-mechanical assembly known to one of skill in the art. Plate 18, plate 18', or both can be affixed to such a mount. This enables individual adjustment at each excitation wavelength if so desired. This enables fine-tuning of the phase between the excitation pattern and the pattern of interference formed by the probe beam 17/reference beam 17' pair over a whole range of wavelengths. Although this does not reduce the measurement wavelength directly, the main effect is that the tolerances on optical components and assembly are greatly relaxed (otherwise the tolerances tend to be much tighter for shorter acoustic wavelengths).

Figure 4A:
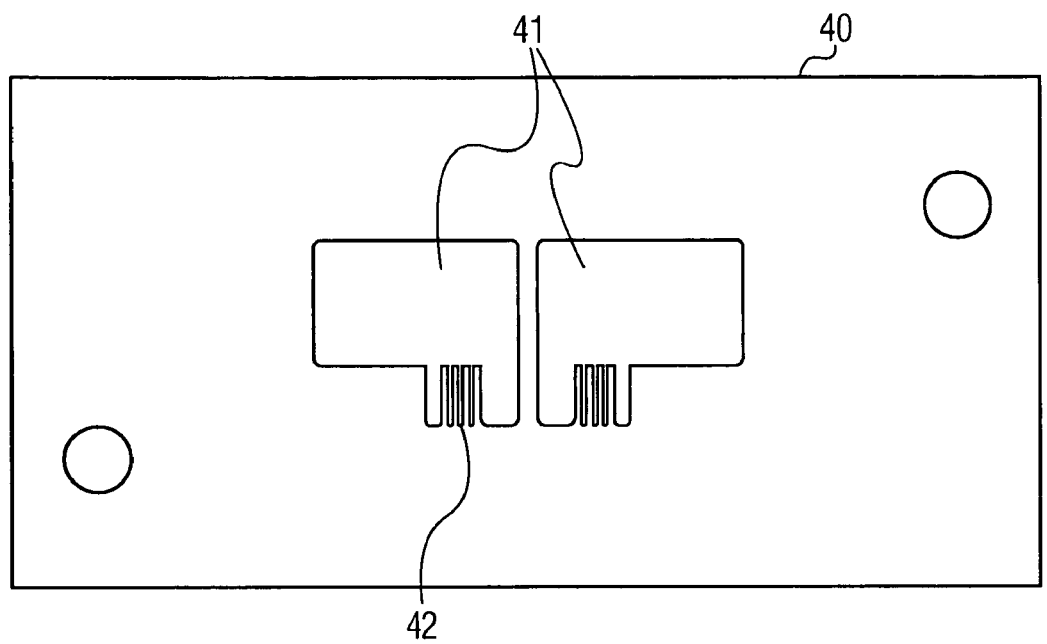
FIG. 4A depicts a fingered aperture beam block.
Figure 5:
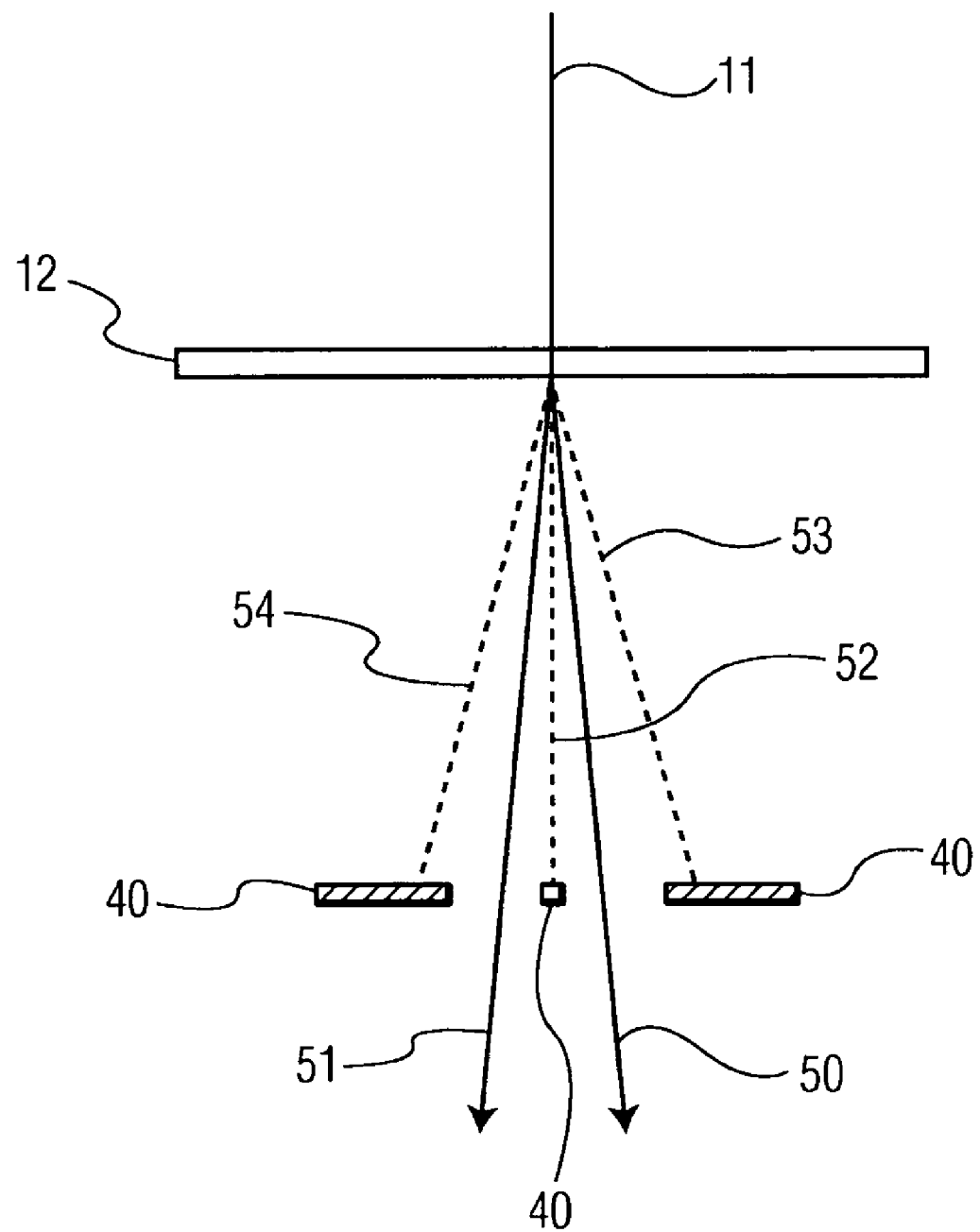
FIG. 5 depicts multiple diffraction order beams from a phase mask, some of them blocked by a beam block.

An additional method of reducing the probing wavelength is to limit the number of diffraction order beams. Reducing the minimum probing wavelength while still keeping the long wavelength capability increases the total wavelength range of the system (consider, for example 4 µm-10 µm range of the prior art system, or 2.5× min-to-max ratio, vs. 1.2 µm-11 µm range of the new system, or 9× min-to-max ratio). Extended wavelength range of the system results in large variation of angles between the excitation and probe sub-beams. Phase grating 12 of FIG. 1 produces multiple diffraction order beams. Only a few of these beams (i.e., the $+1^{st}$ and $-1^{st}$ excitation orders 50, 51) are needed for performing measurement using optical system 1. (See FIG. 5) At least some of the unneeded beams, particularly-, $0^{th\ beam}$ 52, $\pm 3^{rd}$ beams 53 and 54, $\pm 5^{th}$ (not shown), $\pm 7^{th}$ (not shown) etc. excitation orders are undesirable and need to be blocked by the beam block 40 (FIG. 5). FIG. 4A depicts a fingered aperture beam block 40 which blocks undesirable excitation orders. The fingered aperture 41 relies on special ratios of the phase grating 12 periods. The ratios are such that $\pm 1^{st}$ excitation orders always fall between fingers 42 and are transmitted while fingers 42 block all unwanted orders. Within the context of the optical system 1, fingered beam block 40, for example, slides into the appropriate position either between the phase grating 12 and the lens 13 or between the lenses 13 and 14. This only enables the transmission of the $\pm 1^{st}$ excitation orders and blocks the $0^{th}$, $\pm 3^{rd}$ and all higher excitation orders.

Figure 4B:
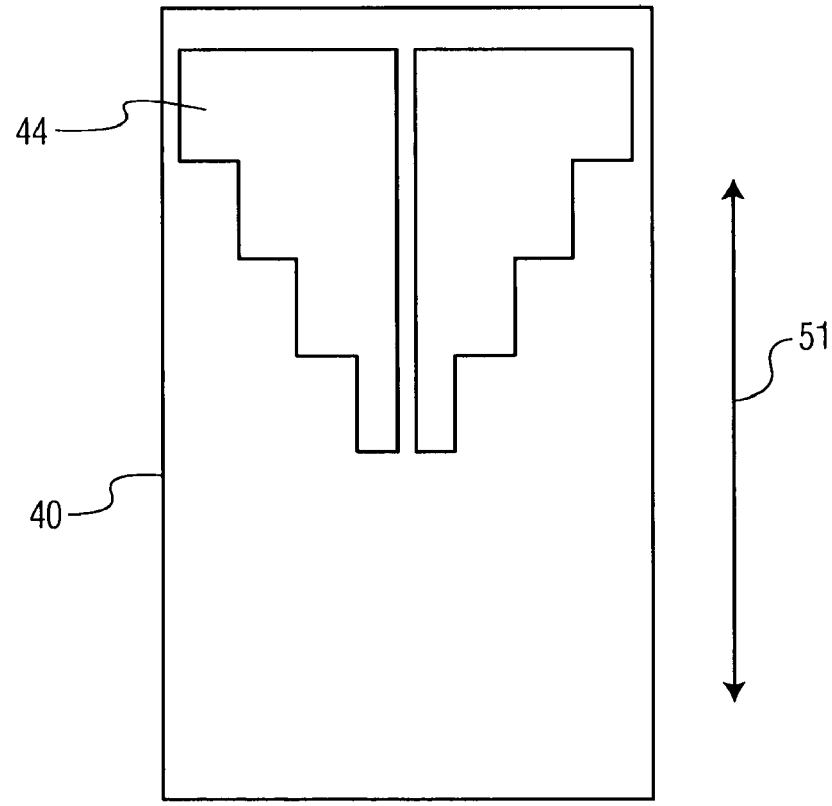
FIG. 4B depicts a moveable aperture beam block.

FIG. 4B depicts an additional example of a moveable aperture beam block 40. Moveable aperture 44 can be slid in and out of the excitation beam's path along arrow 51. The position of the beam block is determined by the resulting measurement wavelength of the instrument and is such the only the needed beams pass through the aperture opening. This may require, for example, a translation slide and/or a motor.

The present invention has been described with respect to particular illustrative embodiments. It is to be understood that the invention is not limited to the above-described embodiments and modifications thereto, and that those of ordinary skill in the art may make various changes and modifications without departing from the spirit and scope of the appended claims.

What is claimed is:

1. An apparatus comprising:
   a first light source 10 that generates an optical excitation pulse 11;
   an optical system 1 aligned to receive the optical excitation pulse 11, separate it into at least two optical sub-pulses 11', 11" and focus at least one sub-pulse 11' onto a surface of a sample 15 to form an excitation pattern with at least one spatial phase and at least one spatial period, wherein said optical system 1 further comprises at least two plates 18, 18', and wherein the tilt of one of the at least two plates 18, 18' can be adjusted in response to a particular excitation wavelength;
   a second light source 16 that generates a probe beam 17 that diffracts off the sample 15;
   an optical detector 19 that detects the diffracted portion of the probe beam 17 to generate a signal; and
   a processor configured to process the signal from the optical detector 19 to determine a property of sample 15, wherein said optical system 1 permits excitation patterns with measurement wavelengths between 1.2 and 11 microns.

2. The apparatus of claim 1, wherein said optical system further comprises an achromat doublet lens 20 comprising a low refractive index element 22 and a high refractive index element 21.

3. The apparatus of claim 2, wherein the achromat doublet lens further comprises a truncated gradient-index glass element.

4. The apparatus of claim 2, wherein the achromat doublet lens includes an aspheric surface.

5. The apparatus of claim 1, wherein the achromat doublet lens 20 further comprises a plane cut parallel to the lens axis.

6. The apparatus of claim 1, wherein one of the at least two plates 18, 18' is attached to a mount 30 which is attached to an electro-mechanical assembly which adjusts the tilt of the one of the at least two plates 18, 18' to which it is attached.

7. The apparatus of claim 1, wherein said optical system 1 further comprises a phase grating 12 which produces multiple diffraction order beams, and wherein said optical system 1 further comprises a beam block 40 configured to block at least one excitation beam beyond the $+1^{st}$ and $-1^{st}$ excitation order.

8. A method of measuring a sample 15 comprising:
   irradiating a portion of the sample 15 with an excitation pattern having at least one spatial phase and spatial period;
   diffracting a portion of a probe beam 17 off a surface of the sample 15;
   detecting the diffracted portion of the probe beam with an optical detector 19 to generate a light-induced signal;
   processing the light-induced signal to determine a property of the sample 15,
   wherein the irradiating and diffracting steps further comprise reducing a probing wavelength to between 1 and 1.2 μm,
   wherein the probing wavelength reduces to between 1 and 1.2 μm by employing a truncated achromat doublet lens 20 with a gradient-index-glass element and/or an aspheric surface, adjusting the tilt of at least one plate 18, 18' in response to a particular excitation wavelength, and/or employing a beam block 40 configured to block at least one excitation beam beyond the $+1^{st}$ and $-1^{st}$ excitation order.

9. The apparatus of claim 8, wherein said beam block 40 further comprises either a fingered or moveable configuration.

* * * * *